United States Patent
Huang

(10) Patent No.: US 7,556,724 B2
(45) Date of Patent: Jul. 7, 2009

(54) ELECTROCHEMICAL SENSOR STRIP AND MANUFACTURING METHOD THEREOF

(75) Inventor: Chun-Mu Huang, Sanchung (TW)

(73) Assignee: BioNime Corporation, Dali (TW)

( * ) Notice: Subject to any disclaimer, the term of this patent is extended or adjusted under 35 U.S.C. 154(b) by 856 days.

(21) Appl. No.: 11/054,894

(22) Filed: Feb. 10, 2005

(65) Prior Publication Data

US 2006/0175199 A1 Aug. 10, 2006

(51) Int. Cl.
*G01N 27/327* (2006.01)

(52) U.S. Cl. .................. 204/403.02; 156/60

(58) Field of Classification Search ............ 204/403.01, 204/403.02, 403.03; 156/60
See application file for complete search history.

(56) References Cited

U.S. PATENT DOCUMENTS

| | | | |
|---|---|---|---|
| 5,628,890 A * | 5/1997 | Carter et al. ............ 204/403.05 |
| 5,842,983 A * | 12/1998 | Abel et al. ............... 204/403.1 |
| 5,985,116 A | 11/1999 | Ikeda et al. |
| 5,997,817 A | 12/1999 | Crismore et al. |
| 6,719,887 B2 * | 4/2004 | Hasegawa et al. ...... 204/403.09 |
| 6,773,563 B2 * | 8/2004 | Matsumoto ................. 204/401 |
| 6,830,669 B2 * | 12/2004 | Miyazaki et al. ............ 204/409 |
| 6,896,778 B2 * | 5/2005 | Lauks ........................ 204/400 |
| 2004/0256228 A1 | 12/2004 | Huang |

\* cited by examiner

*Primary Examiner*—Kaj K Olsen
(74) *Attorney, Agent, or Firm*—Volpe and Koenig, P.C.

(57) ABSTRACT

An electrochemical sensor strip is provided. The electrochemical sensor strip includes an insulating substrate having a reaction concavity integrally formed thereon, a cover, an electrochemical reaction layer, and an electrode device. The reaction concavity is peripherally and entirely enclosed by the insulating substrate. The cover partially covers on the reaction concavity by leaving an opening on the reaction concavity. The electrochemical reaction layer is located in the reaction concavity, and the electrode device is located in the reaction concavity for transmitting a signal resulting from an electrochemical reaction performed in the electrochemical reaction layer.

21 Claims, 13 Drawing Sheets

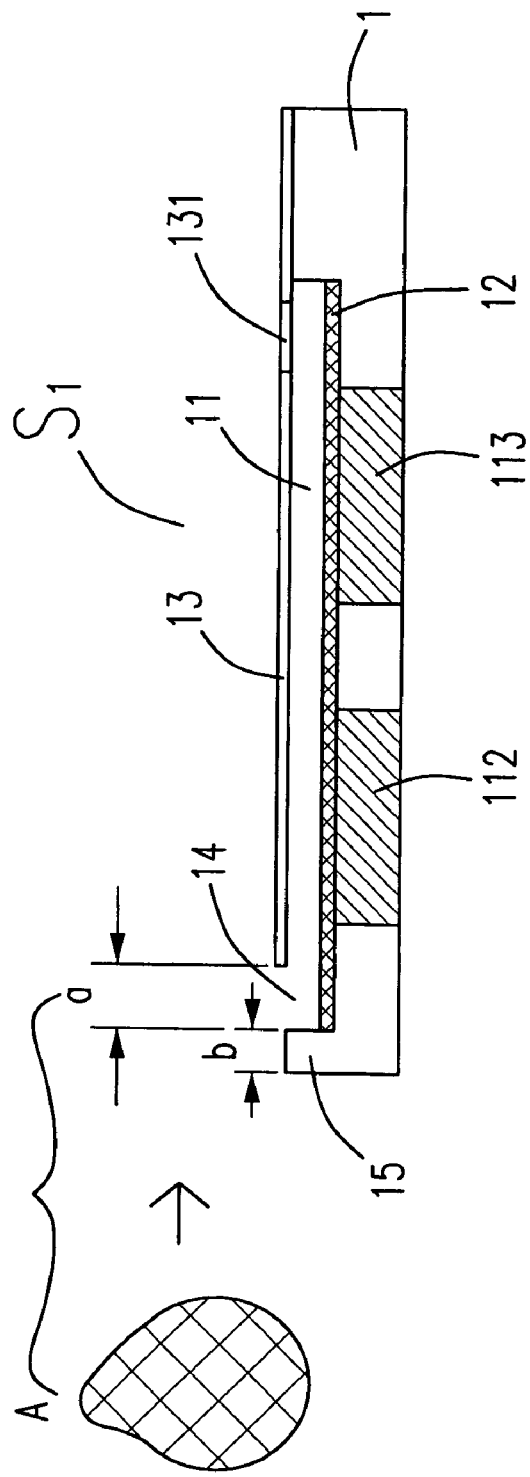
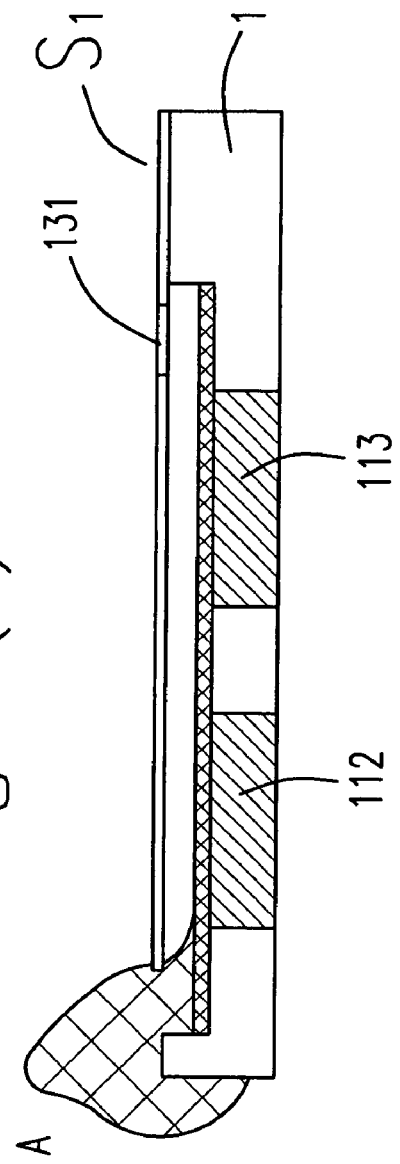
Fig. 5(A)
Fig. 5(B)

ELECTROCHEMICAL SENSOR STRIP AND MANUFACTURING METHOD THEREOF

FIELD OF THE INVENTION

The present invention relates to an electrochemical sensor strip, and more particular to a disposable electrochemical sensor strip. The contents of U.S. Pat. No. 7,063,776 filed on Jun. 17, 2003 are incorporated herewith for reference.

BACKGROUND OF THE INVENTION

The present application is relevant to U.S. patent Ser. No. 10/462,904, and some disposable electrochemical sensor strips with metal electrodes are provided. The electrochemical sensor strips of the present application are suitable for testing the contents of some specific analytes in a sample, especially in a fluid sample. For example, it is possible to test one or more concentrations of glucose, cholesterol, and uric acid in the human blood, or one or more concentrations of the insecticides, pesticides, fungicides, herbicides, heavy metals and so forth in a polluted water by the present invention. In other words, the electrochemical sensor strips according to the present application are suitable to be used in any kind of electrochemical sensors, bio-sensors, fluid biochemical sensors, and some domestic medical sensors (e.g. blood glucose sensor).

In recent decades, the principle of electrochemical sensor has been developed and applied in the field of detecting kinds of fluid ingredients. An electrochemical sensor may be assembled with different equipments due to their different application fields. Nevertheless, an electrochemical sensor in a general laboratory is generally different from that in a professional checking room. A basic framework of an electrochemical sensor includes the following components:

1. A container, which is applied to contain a fluid sample and is a region for measuring an electrochemical reaction;
2. A chemical reagent, which is used for chemically reacting with an analyte contained in the fluid sample and generating an output signal with an electric parameter, wherein the electric parameter is corresponding to an ingredient of the analyte contained in the fluid sample. For example, if the fluid sample is the human blood and the analyte is the glucose, the chemical reagent would be basically a glucose oxidase and a complex thereof;
3. Plural testing electrodes, which are selected from a group consisting of a counter electrode, a working electrode, a reference electrode, and a detecting electrode; and
4. A measuring device, such as an electrochemical meter, which provides the essential working voltage (or current) needed by the electrochemical reaction and measures the electric parameter (output voltage or current) produced by the electrochemical reaction to be recorded for processing the numerical analysis and displaying the testing result thereon.

In general, the plural testing electrodes can include the counter electrode and the working electrode, the reference electrode and the working electrode, or the counter electrode, the working electrode, and the reference electrode. Moreover, a detecting electrode could be included as a fourth electrode, if necessary. The number of the plural testing electrodes is varied according to the requirements of the electrochemical reaction.

The functions of the plural electrodes are mutually different from each other, and the plural electrodes are made of different materials. In the general laboratory, the counter electrode is made of any conductive material, where one of a lower conductive resistance is the better, such as a copper, a silver, a nickel, a graphite, a carbon, a gold, a platinum or other conductive materials, or can be a conductive membrane electrode formed by printing a carbon paste or a silver paste on a conductive material. The most common reference electrode is a modified electrode produced by means of printing or electroplating an Ag/AgCl film. Because the electrochemical electric potential of the Ag/AgCl film is quite stable, it is extensively used as the reference electrode.

The selection of the materials for the working electrodes is more complex and the working electrodes can be categorized as two types according to the used materials. One kind of the working electrode is an electron-transfer mediator modified working electrode, and the other is a metal-catalyzed electrode. The electron-transfer mediator modified working electrode has a chemical reagent immobilized thereon, wherein the chemical reagent includes an enzyme (such as a glucose oxidase) and a redox mediator (such as a potassium ferricyanide, which is extensively used in the glucose testing strip). The enzyme and the analyte will react with each other to produce a new chemical compound (such as $H_2O_2$), the electrons generated from the redox reaction between the electron mediator and the new chemical compound (such as $H_2O_2$) is utilized to produce an electric signal, and through the electrode, the electric parameter corresponding to the electric signal can be outputted. The main purpose of this kind of working electrode is only simply a conductor and is not involved in any chemical catalysis. However, the material used to make the electrodes should be selected specifically, so as to avoid the chemical reaction occurring between the electrodes and the fluid sample or between the electrodes and the chemical reagent thereby interfering the testing result.

The electrode without the chemical interference should be made of an inert conductive material, which is generally a noble metal (such as a gold, a platinum, a palladium, or a rhodium), or a carbon containing material (such as a carbon base screen printing electrode or a graphite bar). Furthermore, because the carbon and the noble metal have no chemical reactivity in a low temperature, the chemical interference would not happen. However, because the noble metal is a little bit expensive, the carbon made electrode is usually applied as the electron-transfer mediator modified working electrode.

As to the metal-catalyzed electrode, it is made of a material which will directly electrochemically react with the chemical reagent, the analyte, or the derivatives thereof, and have an ability of direct catalysis or a function of a single selectivity for the analyte. Thus, no electron mediator is needed to be added into the chemical reagent. This kind of electrode, not like the electrode only needing to be made of a chemically inactive metal, is generally made of a material that must have an ability to catalyze the reaction. Therefore, the material thereof should not be limited to be a noble metal but matched with the analyte, such as a copper, a titanium, a nickel, a gold, a platinum, a palladium, or a rhodium . . . etc., (in which, a rhodium electrode has an excellent ability to directly catalyze $H_2O_2$).

U.S. Pat. No. 5,997,817 had disclosed a metal electrode. In this patent, two conductive metal tracks coated by a palladium are fixed on an insulating substrate for being the metal electrodes (such as a working electrode and a counter electrode). However, the positions that are necessarily formed by palladium are only two tiny sections of the metal electrodes, and the other portions need only be formed by materials having a conductive characteristic rather than being noble metal-palladium. Thus, it would be a waste to coat the palladium onto all the surfaces of the metal electrodes.

In addition, U.S. Pat. No. 5,985,116 had disclosed a disposable printing electrochemical sensor strip. The electrodes on the sensor strip are formed by printing some conductive pastes onto the insulating substrate. However, the sensitivities of the electrodes are determined by the materials of the conductive pastes. If the conductive pastes are made of a noble metal, the sensitivity of the relevant electrodes will be greater, the unnecessary chemical interference would be reduced, but the corresponding cost will be high. On the contrary, in order to decrease the relevant cost, the conductive pastes might be made of a low-cost conductive material, such as the carbon. However, the sensitivity of the relevant electrodes made of a low-cost material will not be so good due to the impedance thereof.

As above, although the use of the electrochemical sensor strips has become the main trend of the domestic medical applications (such as the sensor strips for testing the blood glucose, the uric acid, or the cholesterol contents in the human blood), some problems about the testing accuracy and the relevant cost are still awaiting to be overcome.

Please refer to FIG. 1, which is a flow chart showing the manufacturing process of an electrochemical sensor strip in the prior art. As shown in FIG. 1, the manufacturing process includes the following steps: 1. An insulating substrate is provided. 2. Some electrodes are located on the insulating substrate. 3. A reaction concavity is assembled on the insulating substrate. 4. An electrochemical reaction layer is formed in the reaction concavity by applying a chemical reagent therein. 5. The reaction concavity is sealed after the chemical reagent is dry. 6. An opening located on the side edge of the insulating substrate is formed by a step of eroding.

Please refer to FIGS. 2(A)-2(B), which are the schematic diagrams showing the different statuses of the electrochemical sensor strip during the step of eroding in the prior method. In addition, please refer to FIG. 2(C), which is the schematic diagram showing the status of the fluid sample during the testing step in the prior method. As shown in FIGS. 2(A)-2(C), the electrochemical sensor strip 3 includes the insulating substrate 31, the electrodes 32, the electrochemical layer 33, the reaction cavity 34, the cover 35 and the air hole 37. As shown in FIG. 2(A), the reaction concavity 34 is peripherally and entirely enclosed before a step of eroding. As shown in FIG. 2(B), the opening 36 is formed on the side edge of the electrochemical sensor strip 3 after the electrochemical sensor strip is eroded. In addition, there are some cracks 331 that will be formed due to the mechanical force resulting from the step of see eroding. As shown in FIGS. 2(B)-2(C), however, since there are some cracks 331 on the electrochemical layer 33, it is possible that the testing sample A would be contacted with the electrodes 32 before being reacted with the electrochemical layer 33 so that the electrochemical reaction between the testing sample A and the electrochemical layer 33 might be affected by the cracks 331. As the above discussions, it would be found that the step of eroding is the main reason of the undesired testing accuracy of the electrochemical sensor strip 3.

According to the technical defects described above, for reducing the manufacturing cost of the metal electrode in the sensor strip and overcoming the problems of the structural damage, the applicant has devoted himself to develop another electrochemical sensor strip through a series of experiments, tests and researches. In addition to effectively solving the wasting problem of the noble metal and avoiding the relevant damaging manufacturing procedure in the prior arts, the present application further provides more complete structures of the electrochemical reaction layer for increasing the testing accuracy accordingly. Furthermore, the sensor strip according to the present invention can be applied to kinds of electrochemical testing devices, such as biosensor strips, fluid biochemical sensor strips (e.g., the testing strips for a sewage, a pesticide content, a heavy metal ingredient etc.), and kinds of domestically medical application testing strips (e.g., the testing strips for a blood glucose, a uric acid, and a cholesterol).

SUMMARY OF THE INVENTION

In accordance with an aspect of the present invention, an electrochemical sensor strip is provided. The electrochemical sensor strip includes an insulating substrate having a reaction concavity located thereon and peripherally and entirely enclosed by the insulating substrate, a cover partially covering on the reaction concavity for retaining an opening on the reaction concavity, an electrochemical reaction layer located in the reaction concavity, and an electrode device located in the reaction concavity for transmitting a signal resulting from an electrochemical reaction performed in the electrochemical reaction layer.

Preferably, a distance between a side of the reaction concavity and an edge of the insulating substrate is in a range from 0.1 mm to 3.0 mm.

Preferably, the electrode device has a first end connected to the electrochemical reaction layer and a second end connected to a measuring device for transmitting the signal into the measuring device.

Preferably, the reaction concavity includes at least a hole.

Preferably, the electrode device passes through the hole.

Preferably, the electrode device includes plural electrodes selected from a group consisting of a counter electrode, a working electrode, a reference electrode and a detecting electrode.

Preferably, each of the plural electrodes includes a metal and a thin film.

Preferably, the metal is one selected from a group consisting of a copper, a titanium, a nickel, a gold, a platinum, a rhodium, a palladium, a ruthenium, a silver, a chromium, an iron, an aluminum, an iridium and an alloy thereof.

Preferably, the metal is one selected from a group consisting of a brass, an oxygen-free copper, a bronze, a phosphorized copper, a nickel silver copper and a beryllium copper.

Preferably, the thin film is made of one selected from a group consisting of a copper, a titanium, a nickel, a gold, a platinum, a rhodium, a palladium, a ruthenium, a silver, a chromium, an iron, an aluminum, an iridium and an alloy thereof.

Preferably, each of the plural electrodes includes a carbon body and a thin film.

Preferably, the electrochemical reaction layer further includes a chemical agent for reacting with an analyte of a sample to generate the signal.

Preferably, the sample is added into the reaction concavity via the opening.

Preferably, the insulating substrate is made of one selected from a group consisting of a polyvinyl chloride (PVC), a polypropylene (PP), a polycarbonate (PC), a polybutylene terephthalate (PBT), a polyethylene terephthalate (PET), a modified polyphenylene oxide (PPO) and an acrylonitrile butadiene styrene (ABS).

Preferably, the cover further includes an air hole.

Preferably, the reaction concavity and the insulating substrate are formed integrally.

Preferably, a size of the opening is in a range from 0.1 mm to 3.0 mm.

In accordance with another aspect of the present invention, a method for manufacturing an electrochemical sensor strip is provided. The manufacturing method includes steps of a)

providing an insulating piece having a reaction concavity formed thereon and peripherally and entirely enclosed by the insulating piece, b) locating at least an electrode device in the reaction concavity, c) forming a reaction layer connected to the electrode device in the reaction concavity, and d) partially covering the reaction concavity to remain an opening on the reaction concavity.

Preferably, the reaction concavity and the insulating substrate are formed integrally.

Preferably, the reaction layer is formed by applying a chemical reagent in the reaction concavity.

Preferably, the reaction layer is formed by coating the chemical reagent in the reaction concavity.

Preferably, the reaction layer is formed by dropping the chemical reagent in the reaction concavity.

Preferably, the reaction layer is formed by spreading the chemical reagent in the reaction concavity.

In accordance with another aspect of the present invention, an electrochemical sensor strip is provided. The electrochemical sensor strip includes an insulating substrate having a reaction concavity integrally formed thereon, a cover covering on the reaction concavity for forming an opening, an electrochemical reaction layer located in the reaction concavity, and an electrode device located in the reaction concavity for transmitting a signal resulting from an electrochemical reaction performed in the electrochemical reaction layer. The reaction concavity includes a first area and a second area. The second area is adjacent to the opening and has a second coarseness lower than the coarseness of the first area.

Preferably, the second area includes a width ranged from 0.1 to 2.0 mm.

Preferably, the electrode device has a first end connected to the electrochemical reaction layer and a second end connected to a measuring device for transmitting the signal into the measuring device.

Preferably, the reaction concavity includes at least a hole.

Preferably, the electrode device passes through the hole.

Preferably, the electrode device includes plural electrodes selected from a group consisting of a counter electrode, a working electrode, a reference electrode and a detecting electrode, and each of the electrodes includes a metal and a thin film.

Preferably, the cover further includes an air hole.

Preferably, an edge portion of the insulating substrate is uneven.

The above contents and advantages of the present invention will become more readily apparent to those ordinarily skilled in the art after reviewing the following detailed descriptions and accompanying drawings, in which:

DESCRIPTION OF THE DRAWINGS

FIGS. 5(A)-5(B) are the schematic views showing the steps of testing a sample with the electrochemical sensor strip according to the first embodiment of the present invention;

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
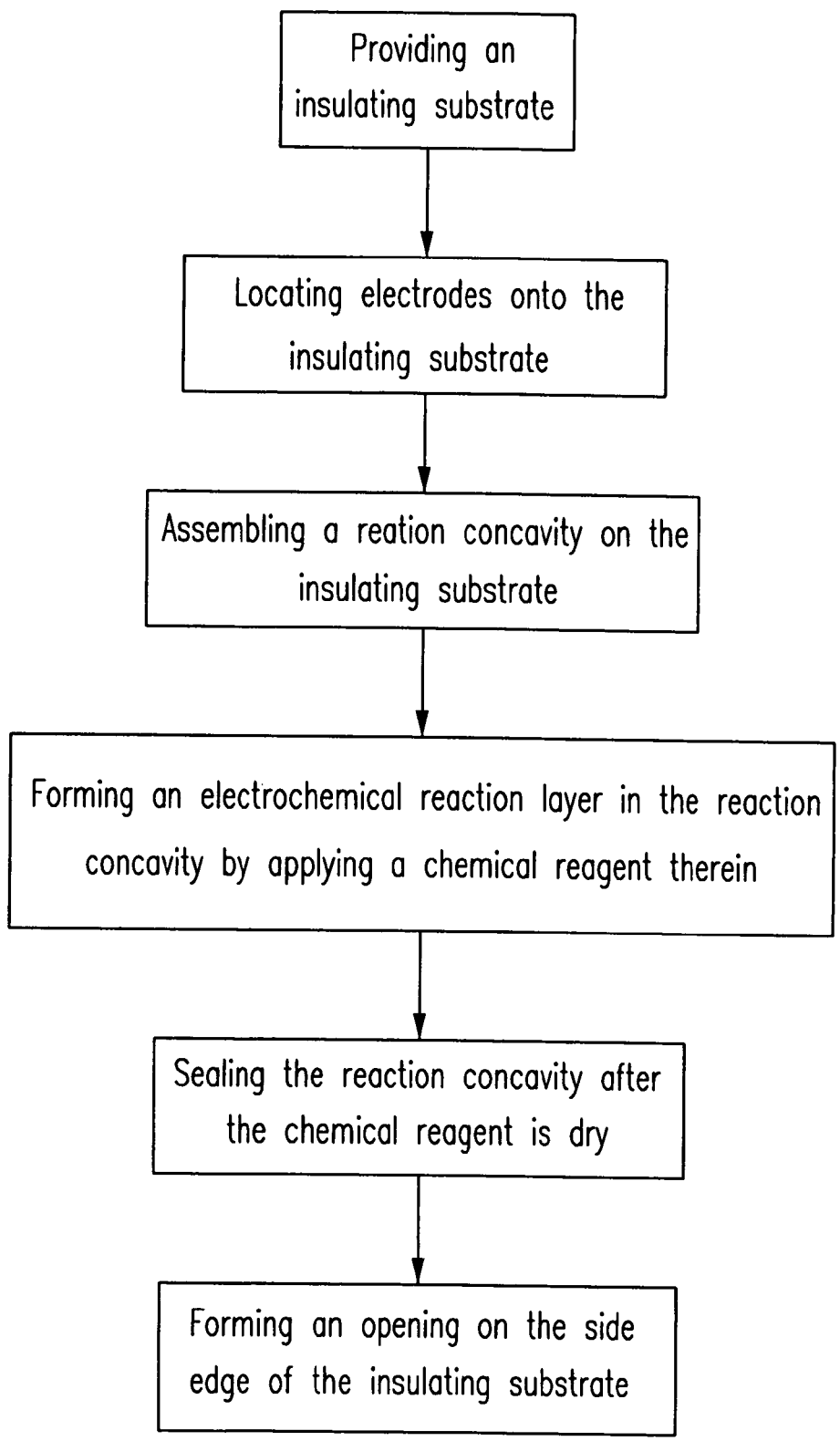
FIG. 1 is a flow chart showing the manufacturing process of an electrochemical sensor strip in the prior art.
Figure 2A:
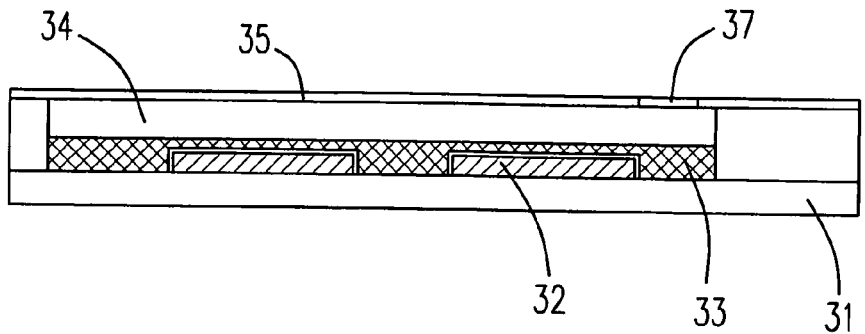
FIGS. 2(A)-2(B) are the schematic diagrams showing the different statuses of the electrochemical sensor strip during the step of see eroding in the prior method.
Figure 2B:
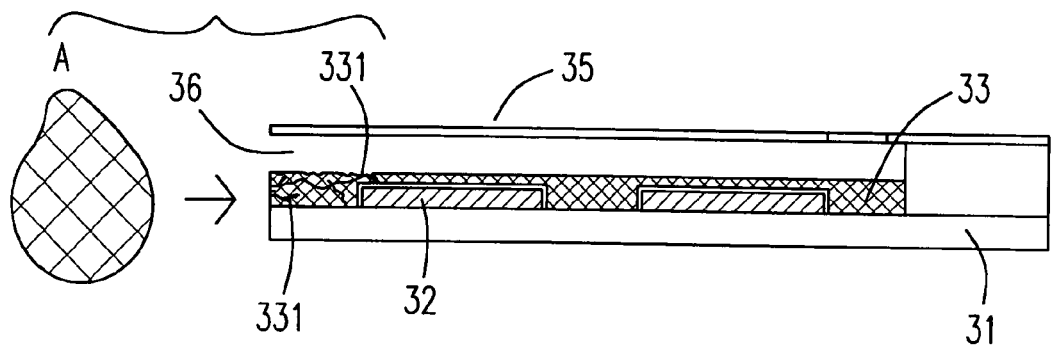
Figure 2C:
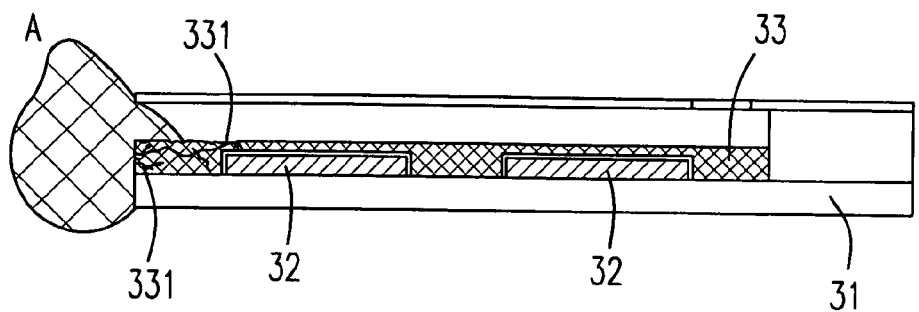
FIG. 2(C) is the schematic diagram showing the status of the fluid simple during the testing step in the prior method.
Figure 3:
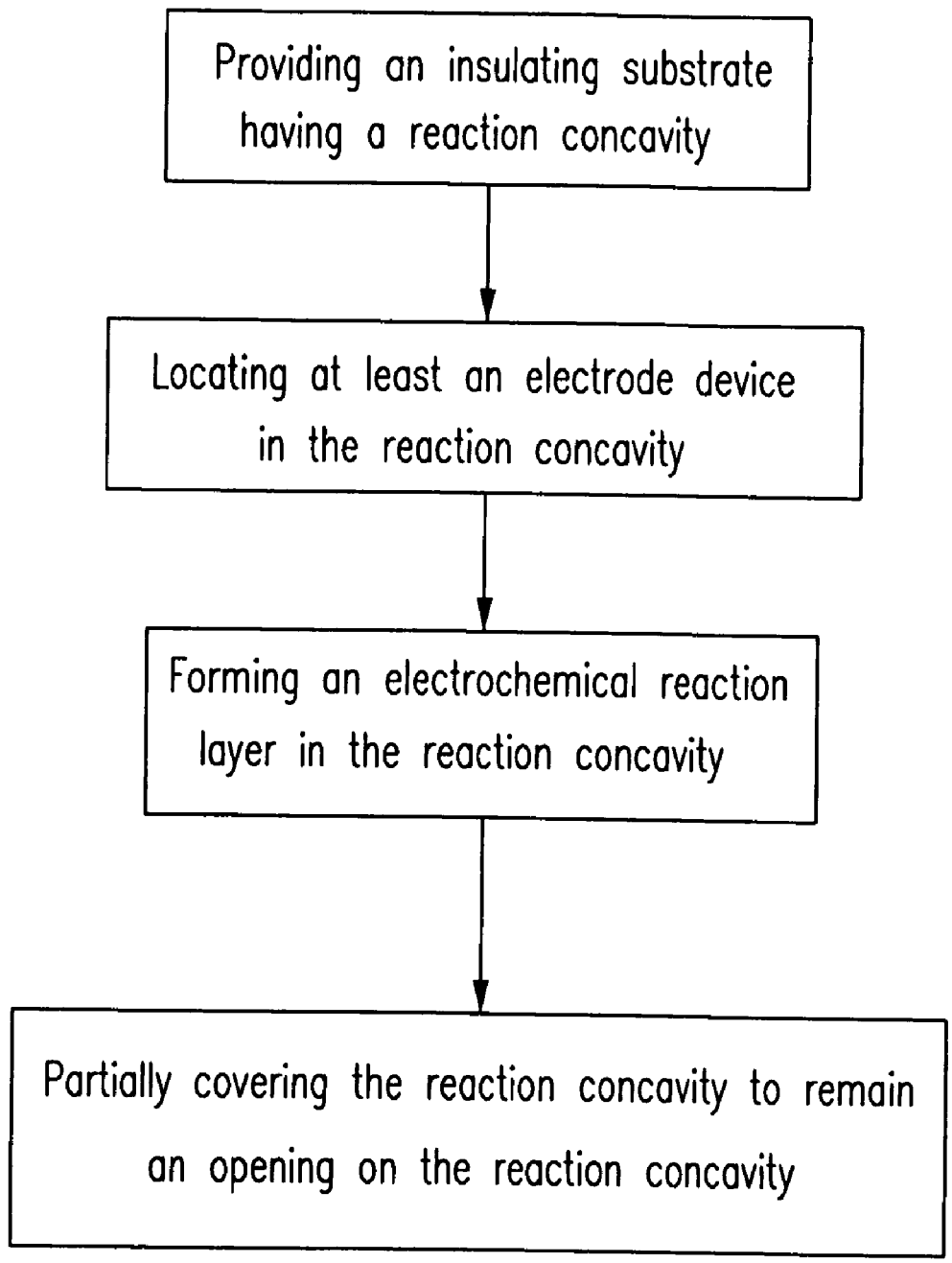
FIG. 3 is a flow chart showing the manufacturing steps of the electrochemical sensor strip according to the present invention.

Please refer to FIG. 3, which is a flow chart showing the manufacturing processes of the electrochemical sensor strip according to the present invention. The manufacturing process includes steps of a) providing an insulating piece having a reaction concavity formed thereon, b) locating at least an electrode device in the reaction concavity, c) forming an electrochemical reaction layer connected to the electrode device in the reaction concavity, and d) partially covering the reaction concavity to leave an opening on the reaction concavity. The reaction layer is formed by coating, spreading, or dropping a chemical reagent in the reaction cavity. The electrode device is formed by plural electrodes and the metal thin films on the plural electrodes. The plural electrodes are made of a metal, an alloy, a carbon or other conductive material. In general, the electrode is made of one selected from a group consisting of a copper, a titanium, a nickel, a gold, a platinum, a rhodium, a palladium, a ruthenium, an iridium, a silver, a chromium, an iron, an aluminum and an alloy thereof. In general, the metal thin films are made of one selected from a group consisting of a copper, a titanium, a nickel, a gold, a platinum, a rhodium, a palladium, a ruthenium, a silver, a chromium, an iron, an aluminum, an iridium and an alloy thereof. In general, the insulating substrate is made of one selected from a group consisting of a polyvinyl chloride (PVC), a polypropylene (PP), a polycarbonate (PC), a polybutylene terephthalate (PBT), a polyethylene terephthalate (PET), a modified polyphenylene oxide (PPO) and an acrylonitrile butadiene styrene (ABS). Since the electrochemical sensor strip of the present invention is formed by combining the components having particular structures, the step of eroding in the prior manufacturing method is successfully dispended with. Therefore, the reaction layer in the electrochemical sensor strip of the present invention will not be damaged by the unnecessary stress resulting from the step eroding.

Figure 4A:
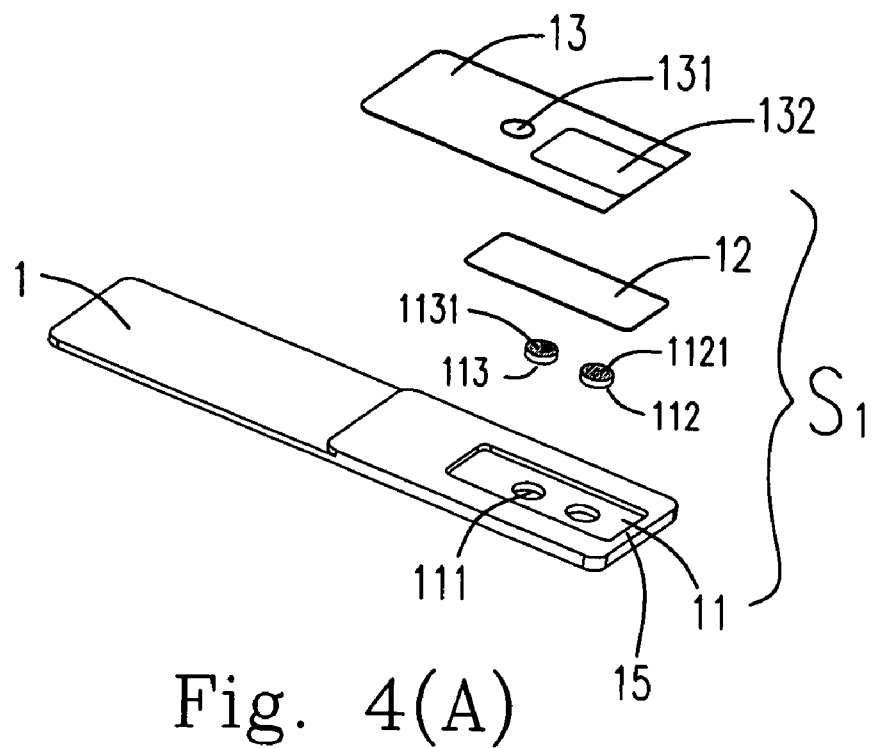
FIG. 4(A) is an exploded view of the disposable electrochemical sensor strip according to the first embodiment of the present invention.
Figure 4B:
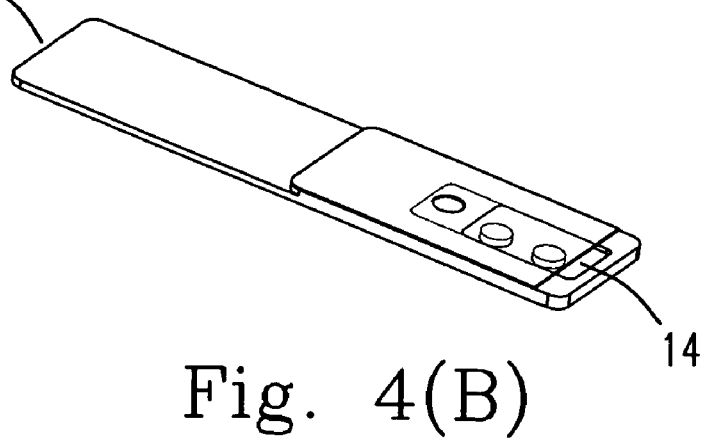
FIG. 4(B) is a schematic view of the disposable electrochemical sensor strip according to the first embodiment of the present invention.
Figure 4C:
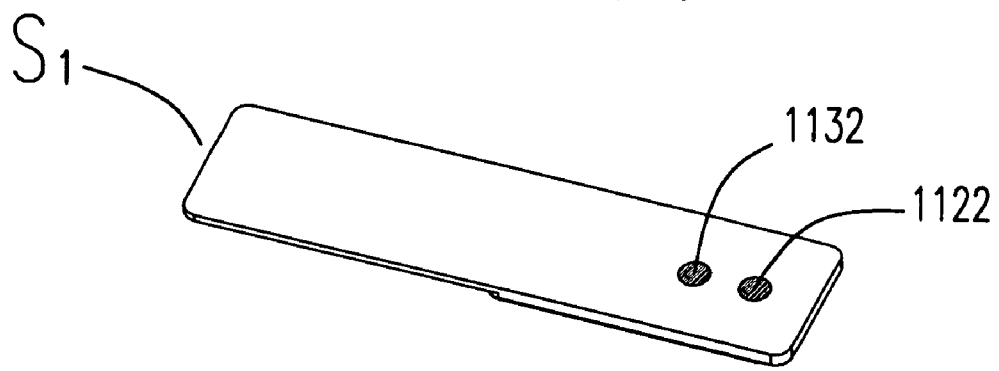
FIG. 4(C) is the back view of the disposable electrochemical sensor strip according to the first embodiment of the present invention.

Please refer to FIGS. 4(A)-4(C). FIG. 4(A) is an exploded view of the disposable electrochemical sensor strip according to the first embodiment of the present invention. FIG. 4(B) is the schematic view of the disposable electrochemical sensor strip according to the first embodiment of the present invention. FIG. 4(C) is the back view of the disposable electrochemical sensor strip according to the first embodiment of the present invention. As shown in FIGS. 4(A)-4(C), the electrochemical sensor strip $S_1$ includes the insulating substrate 1, the reaction concavity 11 located on the insulating substrate 1, the electrochemical reaction layer 12, the cover 13, the opening 14, and the side 15. In which, the cover 13 further includes a ventilator 131 and a window 132, and partially covers the reaction concavity 11. In addition, there are two holes 111 located at the bottom of the reaction concavity 11, and the counter electrode 112 and the working electrode 113 respectively pass through the holes 111. There are metal films 1121 and 1122 on the end surfaces of the counter electrode 112, and there are metals films 1131 and 1132 on the end surfaces of the working electrode 113, wherein the metal films 1121 and 1131 are connected to the electrochemical reaction layer 12 for testing the electrochemical reaction happening in the electrochemical reaction 12. Since the electrochemical sensor strip $S_1$ of the present invention has the side 15 and the opening 14, the prior step of eroding for providing an opening is omitted. Therefore, it is possible to assure the structural completeness of the electrochemical reaction layer 12, and the testing accuracy thereof is increased accordingly. It should be noted that the positions and the shapes of the reaction concavity 11 and the cover 13 should not be limited to the disclosures of this embodiment.

Please refer to FIGS. 5(A)-5(B), which are schematic views showing the processes of testing a sample with the electrochemical sensor strip according to the first embodiment of the present invention. As shown in FIGS. 5(A)-5(B), when a sample A gets into the reaction concavity 11 through the opening 14, an electrochemical reaction will happen between the sample A and the chemical compositions contained in the electrochemical reaction layer 12. During the electrochemical reaction, the ventilator 131 is applied to exhaust the redundant air in the reaction concavity 11 so as to maintain the pressure balance between the inner air of the reaction concavity 11 and the outer air thereof. There is a transparent membrane mounted in the window 132 for observing the movement of the sample A and the electrochemical reaction in the reaction concavity 11. The width b of the side 15 is in a range from 0.1 mm to 3.0 mm, wherein the preferable range is from 0.2 mm to 0.6 mm. The width a of the opening 14 is in a range from 0.1 mm to 3.0 mm, wherein the preferable range is from 0.2 mm to 1.2 mm. Since the side 15 is so narrow that it is easy for a fluid sample A to flow the side 15 and get contact with the opening 14. In addition, since some air will be exhausted via the ventilator 131, the fluid sample A will get into the reaction concavity 11 due to the capillarity. Furthermore, the counter electrode 112 is able to be replaced by a reference electrode, and some detecting electrodes are able to be located on the electrochemical sensor strip $S_1$, if necessary. Nowadays, in general, the electrodes and the metal films are made of one material selected from a group consisting of a copper, a titanium, a nickel, a gold, a platinum, a rhodium, a palladium, a ruthenium, a silver, a chromium, an iron, an aluminum, an iridium and an alloy thereof. In which, a brass, an oxygen-free copper, a bronze, a phosphorized copper, a nickel silver copper and a beryllium copper are the most commonly used materials. Because the end surfaces of the electrodes should have the high sensitivity and stability, and the requirements of the sensitivity and the stability of the other portions of the electrodes are not so strict, only the end surfaces of the electrodes are necessarily formed by the noble metal and the other portions could be formed by general metals or the carbon for reducing the relevant cost. In addition, since the insulating substrate 1 and the reaction concavity 11 are formed integrally via the plastic injection molding, the relevant costs spent on stacking the elements are reduced.

Figure 6A:
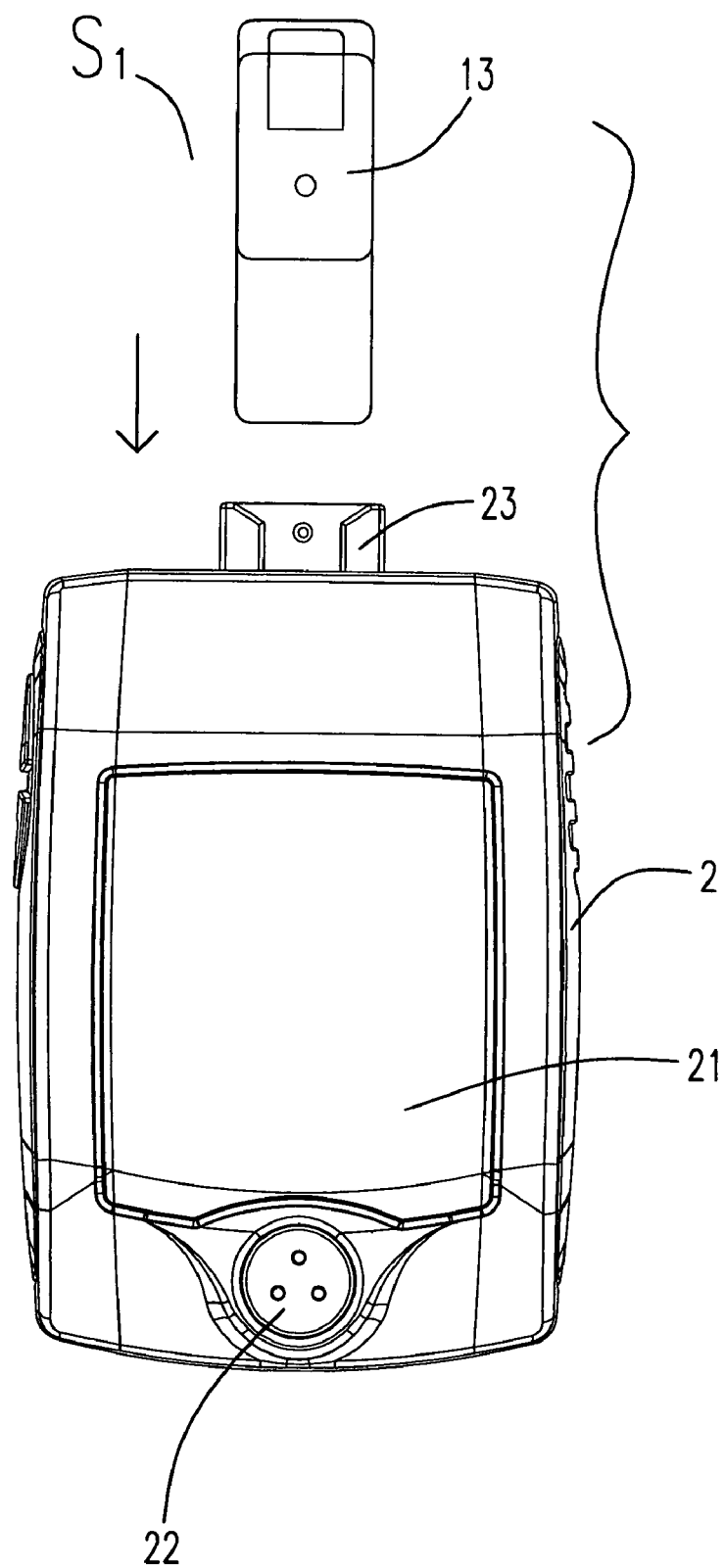
FIGS. 6(A)-6(B), which are the perspective views showing the combination of the sensor and the electrochemical sensor strip according to the first embodiment of the present invention.
Figure 6B:
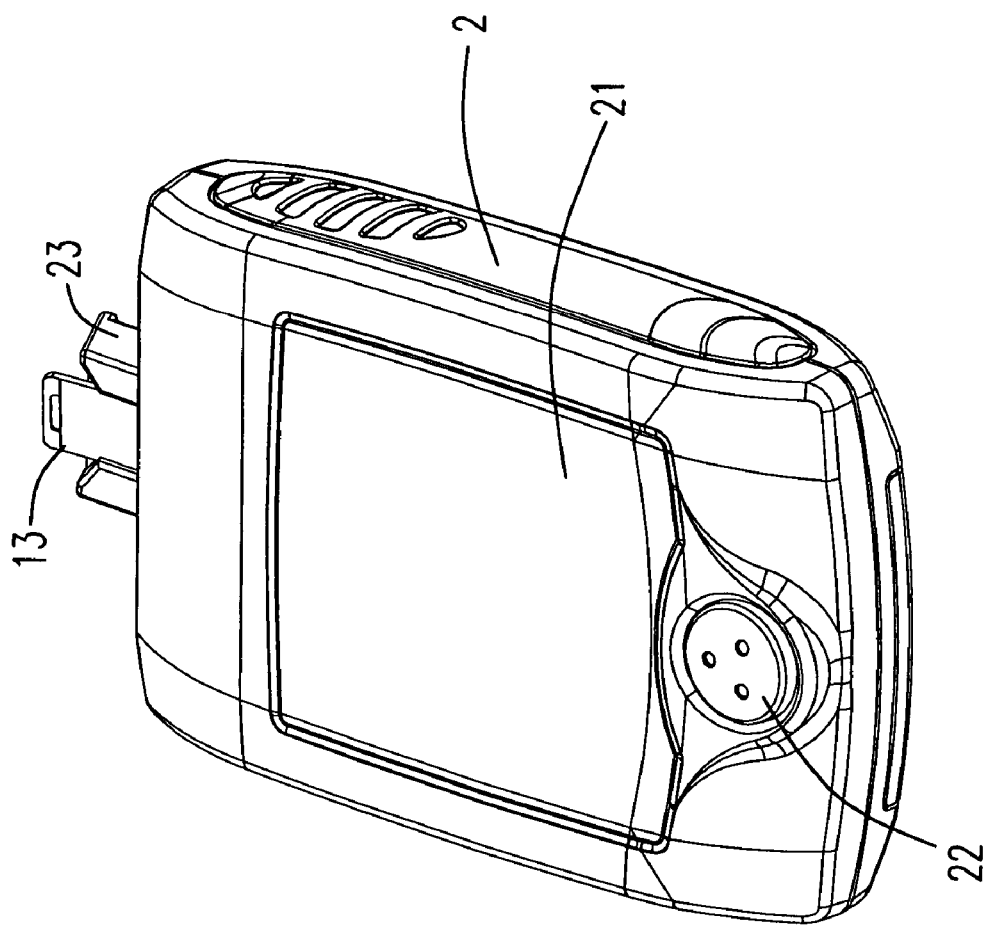

Please refer to FIGS. 6(A)-6(B), which are schematic views showing the combination of the sensor and the electrochemical sensor strip according to the first embodiment of the present invention. As shown in FIGS. 4(A)-6(B), when the electrochemical sensor strip $S_1$ is combined to the sensor 2, the signal resulting from the electrochemical reaction happening in the electrochemical reaction layer 12 would be transmitted to the sensor 2 via the metal films 1122 and 1132. And then the sensor 2 will measure the transmitted signal for being figured out the corresponding value. The sensor 2 includes a display 21 for showing the figured out value, a control key for controlling the sensor 2, and a connecting device 23.

Figure 7A:
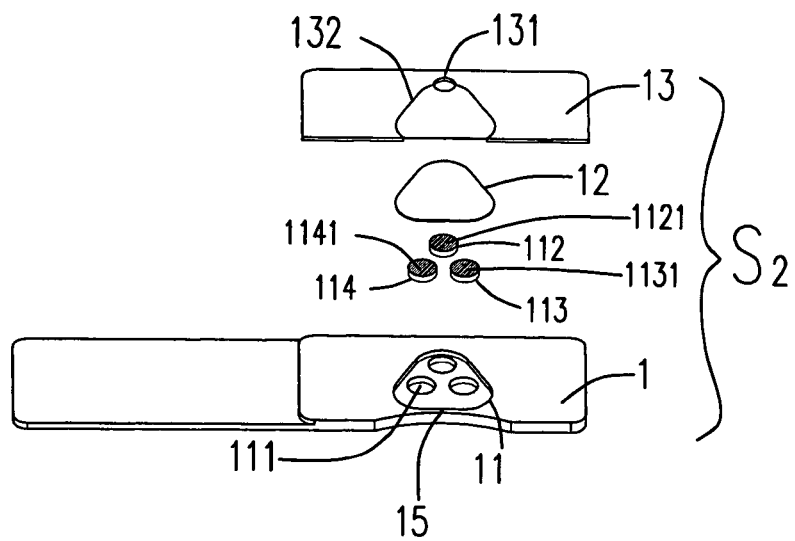
FIG. 7(A) is an exploded view of the disposable electrochemical sensor strip according to the second embodiment of the present invention.
Figure 7B:
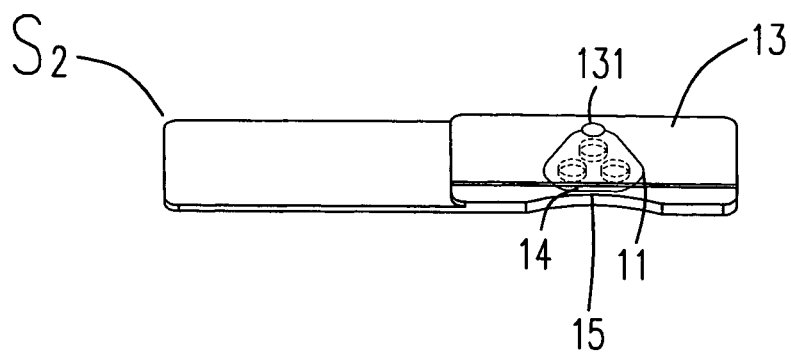
FIG. 7(B) is a perspective view of the disposable electrochemical sensor strip according to the second embodiment of the present invention.
Figure 7C:
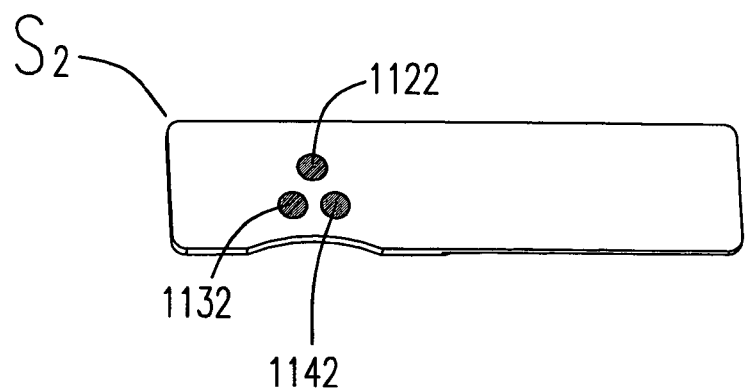
FIG. 7(C) is the back view of the disposable electrochemical sensor strip according to the second embodiment of the present invention.

Please refer to FIGS. 7(A)-7(C). FIG. 7(A) is an exploded view of the disposable electrochemical sensor strip according to the second embodiment of the present invention. FIG. 7(B) is a schematic view of the disposable electrochemical sensor strip according to the second embodiment of the present invention. FIG. 7(C) is the back view of the disposable electrochemical sensor strip according to the second embodiment of the present invention. As shown in FIGS. 7(A)-7(C), the electrochemical sensor strip $S_2$ includes the insulating substrate 1, the reaction concavity 11 located on the insulating substrate 1, the electrochemical reaction layer 12, the cover 13, the opening 14, and the side 15. In which, the cover 13 further includes a ventilator 131 and a window 132, and partially covers the reaction concavity 11. In addition, there are three holes 111 located at the bottom of the reaction concavity 11, and the counter electrode 112, the working electrode 113, and the reference electrode 114 that respectively pass through the holes 111. There are metal films 1121 and 1122 on the end surfaces of the counter electrode 112, there are metals films 1131 and 1132 on the end surfaces of the working electrode 113, and there are metal films 1141 and 1142 on the end surfaces of the reference electrode 114, wherein the metal films 1121, 1131 and 1141 are connected to the electrochemical reaction layer 12 for testing the electrochemical reaction happening in the electrochemical reaction 12. Since the electrochemical sensor strip $S_2$ of the present invention has the side 15 and the opening 14, the prior step of eroding for providing an opening is omitted. Therefore, it is possible to assure the structural completeness of the electrochemical reaction layer 12, and the testing accuracy thereof is increased accordingly. Furthermore, the width of the side 15 is in a range from 0.1 mm to 3.0 mm, wherein the preferable range is from 0.2 mm to 0.6 mm. The width of the opening 14 is in a range from 0.1 mm to 3.0 mm, wherein the preferable range is from 0.2 mm to 1.2 mm. Since the side 15 is so narrow that it is easy for a fluid sample (not shown) to flow through the side 15 and get contact with the opening 14. In addition, since some air will be exhausted via the ventilator 131, the fluid sample will get into the reaction concavity 11 due to the capillarity. It should be noted that the positions and the shapes of the reaction concavity 11 and the cover 13 should not be limited to the disclosures of this embodiment.

As shown in FIGS. 7(A)-7(B), when a sample (not shown) gets into the reaction concavity 11 through the opening 14, an electrochemical reaction will happen between the sample and the chemical compositions contained in the electrochemical reaction layer 12. During the electrochemical reaction, the ventilator 131 is applied to exhaust the redundant air in the reaction concavity 11 so as to maintain the pressure balance between the inner air of the reaction concavity 11 and the outer air thereof and the sample is able to be filled in the reaction concavity 11. There is a transparent membrane mounted in the window 132 for observing the movement of the sample and the electrochemical reaction in the reaction concavity 11. Furthermore, some detecting electrodes are able to be located on the electrochemical sensor strip $S_2$, if necessary. Nowadays, in general, the electrodes and the metal films are made of one material selected from a group consisting of a copper, a titanium, a nickel, a gold, a platinum, a rhodium, a palladium, a ruthenium, a silver, a chromium, an iron, an aluminum, an iridium and an alloy thereof. In which, a brass, an oxygen-free copper, a bronze, a phosphorized copper, a nickel silver copper and a beryllium copper are the most commonly used materials. Because the end surfaces of the electrodes should have the high sensitivity and stability, and the requirements of the sensitivity and the stability of the other portions of the electrodes are not so strict, only the end surfaces of the electrodes are necessarily formed by the noble metal and the other portions could be formed by general metals or the carbon for reducing the relevant cost. In addition, since the insulating substrate 1 and the reaction concavity 11 are formed integrally via the plastic injection molding, the relevant costs spent on the stacking the elements are reduced.

Figure 8A:
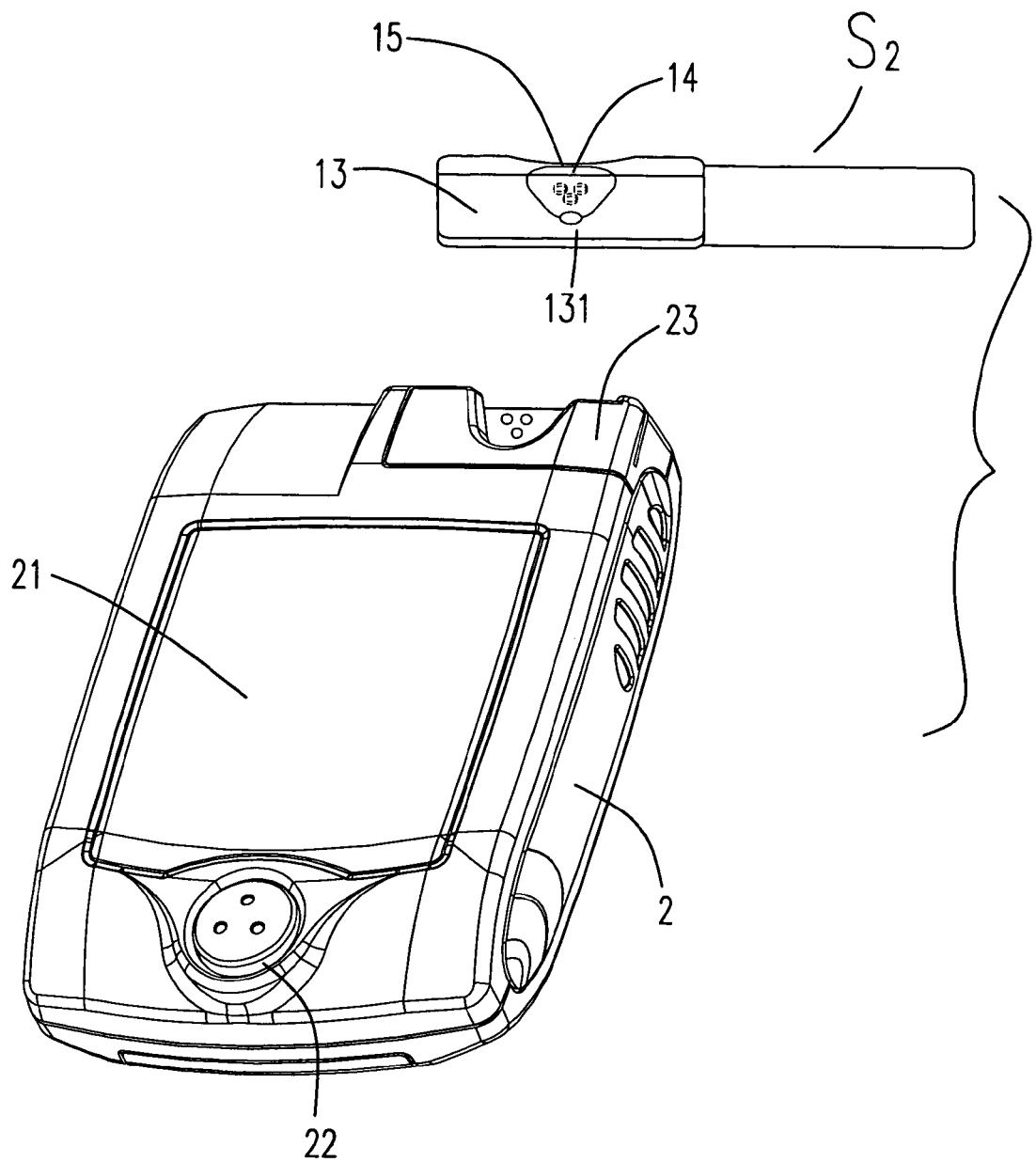
FIGS. 8(A)-8(B) are perspective views showing the combination of the sensor and the electrochemical sensor strip according to the second embodiment of the present invention.
Figure 8B:
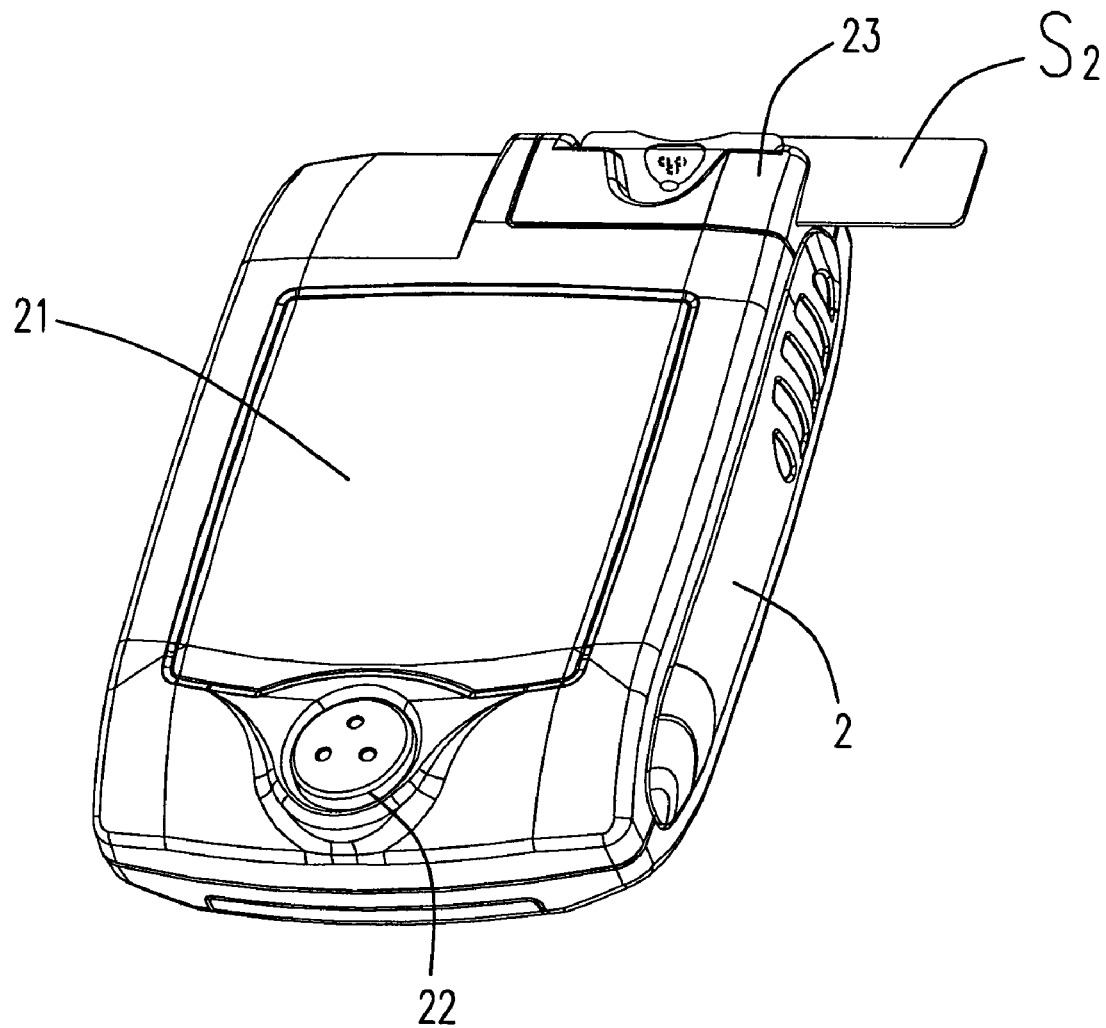

Please refer to FIGS. 8(A)-8(B), which are schematic views showing the combination of the sensor and the electrochemical sensor strip according to the second embodiment of the present invention. As shown in FIGS. 7(A)-8(B), when the electrochemical sensor strip $S_2$ is combined to the sensor 2, the signal resulting from the electrochemical reaction happening in the electrochemical reaction layer 12 would be transmitted to the sensor 2 via the metal films 1122, 1132 and 1142. And then the sensor 2 will measure the transmitted signal for being figure out the corresponding value. The sensor 2 includes a display 21 for showing the figured out value, a control key for controlling the sensor 2, and a connecting device 23.

Figure 9A:
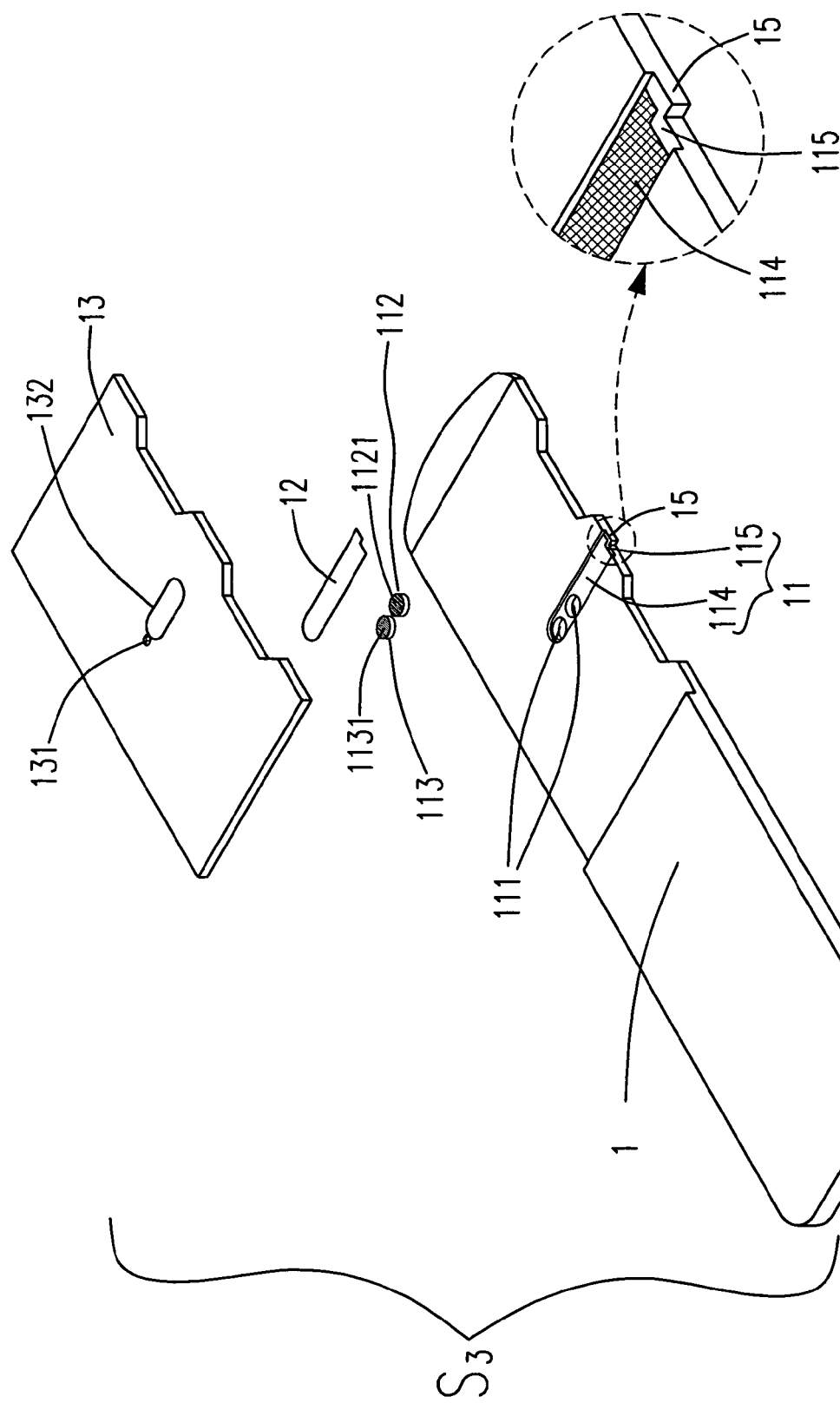
FIG. 9(A) is an exploded view of the disposable electrochemical sensor strip according to the third embodiment of the present invention.
Figure 9B:
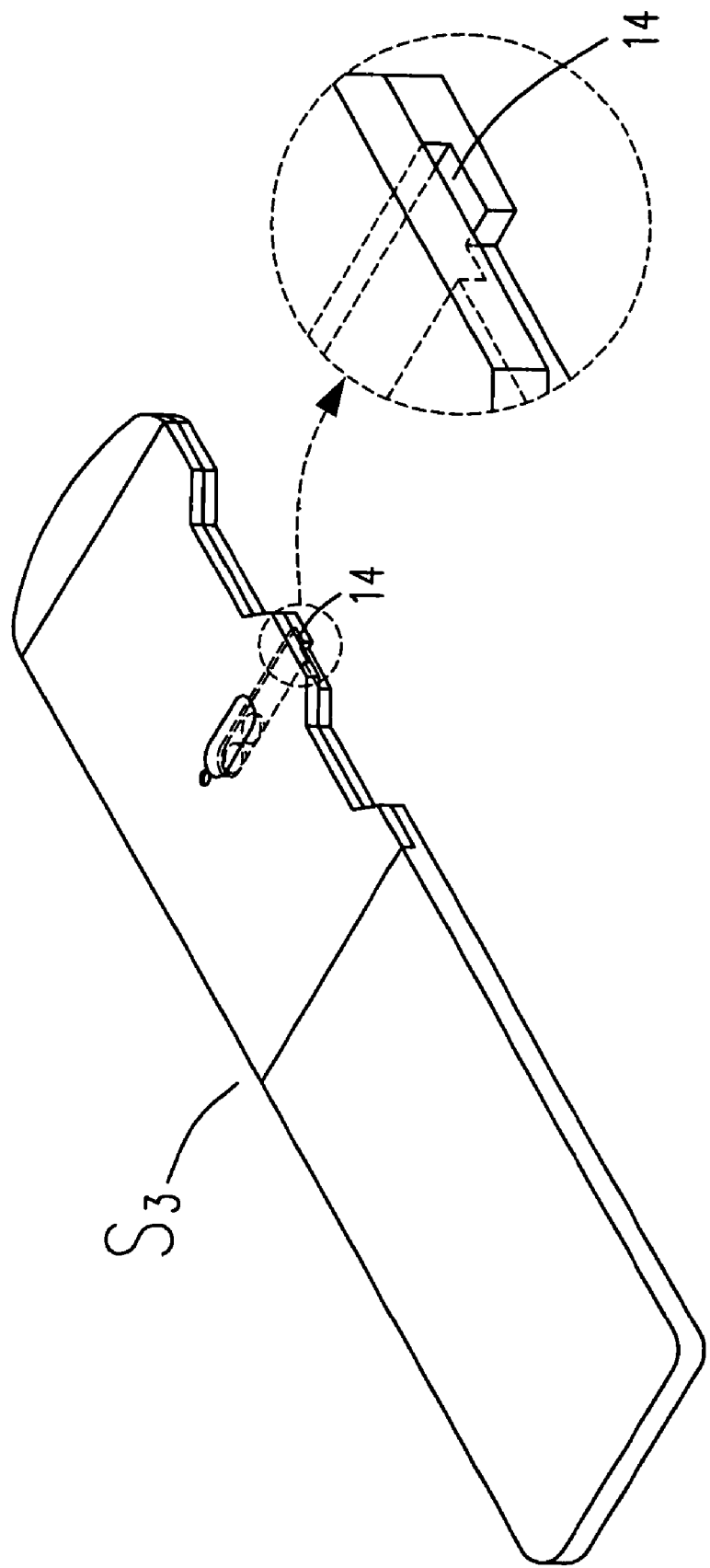
FIG. 9(B) is a perspective view of the disposable electrochemical sensor strip according to the third embodiment of the present invention.
Figure 9C:
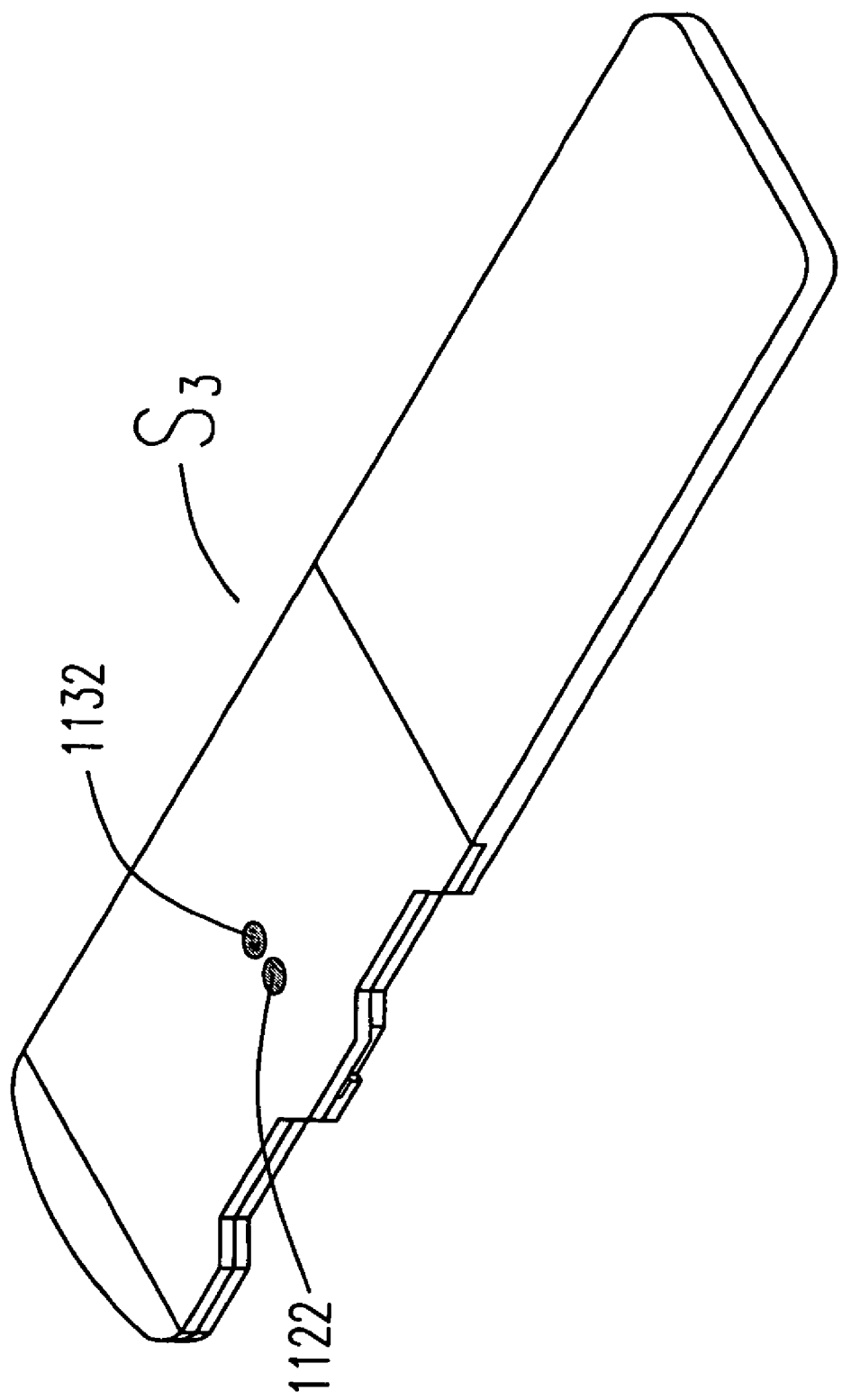
FIG. 9(C) is the back view of the disposable electrochemical sensor strip according to the third embodiment of the present invention.

Please refer to FIGS. 9(A)-9(C). FIG. 9(A) is an exploded view of the disposable electrochemical sensor strip according to the third embodiment of the present invention. FIG. 9(B) is a schematic view of the disposable electrochemical sensor strip according to the third embodiment of the present invention. FIG. 9(C) is the back view of the disposable electrochemical sensor strip according to the third embodiment of the present invention. As shown in FIG. 9(A), the electrochemical sensor strip S.sub.3 includes the insulating substrate 1, the reaction concavity 11 integrally formed on the insulating substrate 1, the electrochemical reaction layer 12, the cover 13 and the uneven side 15. In which, the cover 13 further includes a ventilator 131 and a window 132, and the opening 14 would be formed by the cover 13 and the substrate 1 (please refer to FIG. 9(B)). In addition, there are two holes 111 located at the bottom of the reaction concavity 11, and the counter electrode 112 and the working electrode 113 respectively pass through the holes 111. The reaction concavity 11 further includes the first area 114 and the second area 115. In general, the width of the second area is ranged from 0.1 to 2.0 mm. In practice, it is general that there will be a height difference between the first area 114 and the second area 115. The coarseness of the first area 114 (a so-called coarse area) is higher than that of the second area 115 (a so-called polish area) so that when a liquid (not shown) enters the reaction concavity 11, it would not easily be leaked out from the first area 114 due to the different surface tensions respectively caused by the first area 114 with the liquid and by the second area 115 with the liquid. Please refer to FIGS. 9(A) and 9(C), there are metal films 1121 and 1122 on the end surfaces of the counter electrode 112, and there are metals films 1131 and 1132 on the end surfaces of the working electrode 113, wherein the metal films 1121 and 1131 are connected to the electrochemical reaction layer 12 for testing the electrochemical reaction happening in the electrochemical reaction 12. Since the electrochemical sensor strip S.sub.3 of the present invention has the opening 14 formed by the cover 13 and the substrate 1, the prior step of eroding for providing an opening is omitted. Therefore, it is possible to assure the structural completeness of the electrochemical reaction layer 12, and the testing accuracy thereof is increased accordingly. Furthermore, since the substrate 1 has the uneven side 15, the probability of the whole opening 14 being blocked simultaneously could be effectively reduced and the sample (not shown) could enter the electrochemical reaction layer 12 more easily. It should be noted that the positions and the shapes of the reaction concavity 11 and the cover 13 should not be limited to the disclosures of this embodiment.

As shown in FIGS. 9(A)-9(B), when a sample (not shown) gets into the reaction concavity 11 through the opening 14, an electrochemical reaction will happen among the sample and the chemical compositions contained in the electrochemical reaction layer 12. During the electrochemical reaction, the ventilator 131 is applied to exhaust the redundant air in the reaction concavity 11 so as to maintain the pressure balance between the inner air of the reaction concavity 11 and the outer air thereof and the sample is able to be filled in the reaction concavity 11. There could be a transparent membrane mounted in the window 132 for observing the movement of the sample and the electrochemical reaction in the reaction concavity 11. Furthermore, some detecting electrodes are able to be located on the electrochemical sensor strip $S_3$, if necessary. Nowadays, in general, the electrodes and the metal films are made of one material selected from a group consisting of a copper, a titanium, a nickel, a gold, a platinum, a rhodium, a palladium, a ruthenium, a silver, a chromium, an iron, an aluminum, an iridium and an alloy thereof. In which, a brass, an oxygen-free copper, a bronze, a phosphorized copper, a nickel silver copper and a beryllium copper are the most commonly used materials. Because the end surfaces of the electrodes should have the high sensitivity and stability, and the requirements of the sensitivity and the stability of the other portions of the electrodes are not so strict, only the end surfaces of the electrodes are necessarily formed by the noble metal and the other portions could be formed by general metals or the carbon for reducing the relevant cost. In addition, since the insulating substrate 1 and the reaction concavity 11 are formed integrally via the plastic injection molding, the relevant costs spent on the stacking the elements are reduced.

In view of the aforesaid, the present invention provides a novel manufacturing method of the disposable electrochemical sensor strip, wherein the step of eroding is omitted and the relevant cost is saved. In addition, since the electrochemical sensor strip of the present invention is formed by the components with specific geometric structures and no step of see eroding is necessary, the structural completeness and the relevant testing accuracy of the electrochemical sensor strip are certainly improved. Therefore, the present invention is extremely suitable for being used in the industrial production.

While the invention has been described in terms of what is presently considered to be the most practical and preferred embodiment, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An electrochemical sensor strip, comprising:
    an insulating substrate having a reaction concavity integrally formed with said insulating substrate and located thereon and having a periphery entirely enclosed by said insulating substrate, wherein said reaction concavity has at least one hole at a bottom thereof;
    a cover partially covering on said reaction concavity for leaving an opening on said reaction concavity;
    an electrochemical reaction layer located in said reaction concavity; and
    an electrode device located in said reaction concavity, embedded into said at least one hole and having a first end contacted with said electrochemical reaction layer and a second end contacted with a measuring device for transmitting a signal resulting from an electrochemical reaction performed in said electrochemical reaction layer to said measuring device, wherein said first and second ends are opposite to each other.

2. The electrochemical sensor strip according to claim 1, wherein a distance between a side of said reaction concavity and an edge of said insulating substrate is in a range from 0.1 mm to 3.0 mm.

3. The electrochemical sensor strip according to claim 2, wherein said electrode device comprises plural electrodes selected from a group consisting of a counter electrode, a working electrode, a reference electrode and a detecting electrode.

4. The electrochemical sensor strip according to claim 3, wherein each of said plural electrodes comprises a metal and a thin film.

5. The electrochemical sensor strip according to claim 4, wherein said metal is one selected from a group consisting of a copper, a titanium, a nickel, a gold, a platinum, a rhodium, a palladium, a ruthenium, a silver, a chromium, an iron, an aluminum, an iridium and an alloy thereof.

6. The electrochemical sensor strip according to claim 4, wherein said metal is one selected from a group consisting of a brass, an oxygen-free copper, a bronze, a phosphorized copper, a nickel silver copper and a beryllium copper.

7. The electrochemical sensor strip according to claim 4, wherein said thin film is made of one selected from a group consisting of a copper, a titanium, a nickel, a gold, a platinum, a rhodium, a palladium, a ruthenium, a silver, a chromium, an iron, aluminum, an iridium and an alloy thereof.

8. The electrochemical sensor strip according to claim 3, wherein each of said plural electrodes comprises a carbon body and a thin film.

9. The electrochemical sensor strip according to claim 1, wherein said electrochemical reaction layer further comprises a chemical agent for reacting with an analyte of a sample to generate said signal.

10. The electrochemical sensor strip according to claim 9, wherein said sample is added into said reaction concavity via said opening.

11. The electrochemical sensor strip according to claim 1, wherein said insulating substrate is made of one selected from a group consisting of a polyvinyl chloride (PVC), a polypropylene (PP), a polycarbonate (PC), a polybutylene terephthalate (PBT), a polyethylene terephthalate (PET), a modified polyphenylene oxide (PPO) and an acrylonitrile butadiene styrene (ABS).

12. The electrochemical sensor strip according to claim 1, wherein said cover further comprises an air hole.

13. The electrochemical sensor strip according to claim 1, wherein a size of said opening is in a range from 0.1 mm to 3.0 mm.

14. A method for manufacturing an electrochemical sensor strip, comprising steps of:
    a) providing an insulating piece having a reaction concavity integrally formed thereon and having a periphery entirely enclosed by said insulating piece, wherein said reaction concavity has at least one hole at a bottom thereof;
    b) embedding at least an electrode device having an upper end and a lower end into said at least one hole to make said lower end contact to a measuring device;
    c) forming a reaction layer contacted to said upper end in said reaction concavity; and
    d) partially covering said reaction concavity to leave an opening on said reaction concavity.

15. The method according to claim 14, wherein said reaction layer is formed by applying a chemical reagent in said reaction concavity.

16. An electrochemical sensor strip, comprising:
    an insulating substrate having a reaction concavity integrally formed thereon, wherein said reaction concavity comprises a first area, a second area and at least one hole at a bottom thereof;
    a cover covering on said reaction concavity for forming an opening;
    an electrochemical reaction layer located in said reaction concavity; and
    an electrode device located in said reaction concavity, configured in said at least one hole and having a first surface contacted to said electrochemical reaction layer and a second surface contacted to an external device for transmitting a signal resulting from an electrochemical reaction performed in said electrochemical reaction layer to said external device,
    wherein said second area is adjacent to said opening and said first and second surfaces are opposite to each other.

17. The electrochemical sensor strip according to claim 16, wherein said second area comprises a width ranged from 0.1 to 2.0 mm.

18. The electrochemical sensor strip according to claim 16, wherein said electrode device comprises plural electrodes selected from a group consisting of a counter electrode, a working electrode, a reference electrode and a detecting electrode, and each of said electrodes comprises a metal and a thin film.

19. The electrochemical sensor strip according to claim 16, wherein said cover further comprises an air hole.

20. The electrochemical sensor strip according to claim 16, wherein an edge portion of said insulating substrate is uneven.

21. The electrochemical sensor strip according to claim 16, wherein said second area has a second coarseness lower than a first coarseness of said first area.

* * * * *